(12) United States Patent
Kim et al.

(10) Patent No.: US 11,730,375 B2
(45) Date of Patent: Aug. 22, 2023

(54) PHOTOACOUSTIC, NONINVASIVE, AND CONTINUOUS BLOOD GLUCOSE MEASUREMENT DEVICE

(71) Applicants: HYUNDAI MOTOR COMPANY, Seoul (KR); KIA MOTORS CORPORATION, Seoul (KR); POSTECH ACADEMY-INDUSTRY FOUNDATION, Pohang-si (KR)

(72) Inventors: Eung Hwan Kim, Seoul (KR); Seul Ki Jeon, Suwon-si (KR); Nam Woong Hur, Hwaseong-si (KR); Jin Woo Baik, Daejeon (KR); Jin Young Kim, Pohang-si (KR); Da Yoon Kang, Pohang-si (KR); Chul Hong Kim, Pohang-si (KR)

(73) Assignees: HYUNDAI MOTOR COMPANY, Seoul (KR); KIA MOTORS CORPORATION, Seoul (KR); POSTECH ACADEMY-INDUSTRY FOUNDATION, Pohang-si (KR)

( * ) Notice: Subject to any disclaimer, the term of this patent is extended or adjusted under 35 U.S.C. 154(b) by 372 days.

(21) Appl. No.: 16/984,584

(22) Filed: Aug. 4, 2020

(65) Prior Publication Data
US 2020/0359904 A1  Nov. 19, 2020

Related U.S. Application Data

(62) Division of application No. 15/663,107, filed on Jul. 28, 2017, now abandoned.

(30) Foreign Application Priority Data

Dec. 14, 2016  (KR) .................. 10-2016-0170567

(51) Int. Cl.
*A61B 5/1455* (2006.01)
*A61B 5/00* (2006.01)
*A61B 5/145* (2006.01)

(52) U.S. Cl.
CPC ........ *A61B 5/0095* (2013.01); *A61B 5/14532* (2013.01)

(58) Field of Classification Search
CPC .......................... A61B 5/0095; A61B 5/1455
See application file for complete search history.

(56) References Cited

U.S. PATENT DOCUMENTS 8,306,593 B2   11/2012  Hwang et al.
9,161,742 B2   10/2015  Neasham et al.
(Continued)

FOREIGN PATENT DOCUMENTS

CN   205302556 U   6/2016
CN   105996967 A   10/2016
(Continued)

OTHER PUBLICATIONS

Office Action issued in corresponding Korean Patent Application No. 10-2016-0170567 dated Feb. 18, 2022, with English translation.
(Continued)

*Primary Examiner* — Marjan Fardanesh
(74) *Attorney, Agent, or Firm* — Morgan, Lewis & Bockius LLP

(57) ABSTRACT

A photoacoustic, noninvasive, and continuous blood glucose measurement device includes: a diode laser for irradiating a living body with a pulsed laser signal having a specific wavelength; and an ultrasound transducer for measuring a photoacoustic signal in a form of ultrasonic waves generated by a reaction of the living body with the pulsed laser signal.

3 Claims, 13 Drawing Sheets

(56) References Cited

U.S. PATENT DOCUMENTS

| | | |
|---|---|---|
| 10,433,733 B2 | 10/2019 | Wang et al. |
| 10,542,920 B2 | 1/2020 | Sato |
| 2008/0188724 A1 | 8/2008 | Hwang et al. |
| 2009/0156915 A1 | 6/2009 | Cross |
| 2010/0268042 A1 | 10/2010 | Wang et al. |
| 2013/0245406 A1 | 9/2013 | Wang et al. |
| 2014/0275826 A1 | 9/2014 | Li et al. |
| 2014/0276067 A1 | 9/2014 | Neasham et al. |
| 2016/0009317 A1 | 1/2016 | Evreinov et al. |
| 2016/0081558 A1 | 3/2016 | Wang et al. |
| 2016/0213324 A1 | 7/2016 | Gil et al. |
| 2016/0331240 A1 | 11/2016 | Leahy |
| 2017/0065178 A1 | 3/2017 | Suzuki et al. |
| 2017/0135616 A1 | 5/2017 | Sato |

FOREIGN PATENT DOCUMENTS

| | | | |
|---|---|---|---|
| CN | 106061385 A | | 10/2016 |
| CN | 106163399 A | | 11/2016 |
| JP | 2007-203913 A | | 8/2007 |
| JP | 2009-213637 A | | 9/2009 |
| JP | 2014-184870 A | | 10/2014 |
| KR | 10-2007-0055614 A | | 5/2007 |
| KR | 10-2008-0072158 A | | 8/2008 |
| KR | 10-0871074 B1 | | 11/2008 |
| KR | 10-2014-0006487 A | | 1/2014 |
| KR | 10-2014-0096609 A | | 8/2014 |
| KR | 10-2015-128962 A | | 11/2015 |
| KR | 10-1599479 B1 | | 3/2016 |
| WO | 2009-055705 A2 | | 4/2009 |

OTHER PUBLICATIONS

Notification of the First Office Action issued in corresponding Korean Patent Application No. 201710703558X dated Apr. 8, 2021, with English translation.

Final Office Action issued in corresponding U.S. Appl. No. 15/663,107 dated May 15, 2020.

Office Action issued in corresponding U.S. Appl. No. 15/663,107 dated Oct. 29, 2019.

Office Action issued in corresponding Chinese Patent Application No. 201710703558X dated Aug. 4, 2021, with English translation.

Office Action issued in corresponding German Patent Application No. 10 2017 213 018.0 dated Jan. 16, 2023, with English translation.

PHOTOACOUSTIC, NONINVASIVE, AND CONTINUOUS BLOOD GLUCOSE MEASUREMENT DEVICE

CROSS-REFERENCE TO RELATED APPLICATION

This application is a divisional application of U.S. patent application Ser. No. 15/663,107, filed on Jul. 28, 2017, based on and claims the benefit of priority to Korean Patent Application No. 10-2016-0170567, filed on Dec. 14, 2016, with the Korean Intellectual Property Office, the disclosures of which are incorporated herein in their entirety by reference.

TECHNICAL FIELD

The present disclosure relates to a photoacoustic, noninvasive, and continuous blood glucose measurement device and, more particularly, to a technology for measuring blood glucose of a driver in a short period of time while driving by introducing an inexpensive, noninvasive, and continuous blood glucose sensor into a vehicle.

BACKGROUND

With an increased number of diabetic patients and an increased concern about risks of complications developed from diabetes, a demand for blood glucose measurement devices for long-term blood glucose control is continuously increasing. In particular, if a driver becomes unconscious due to hypoglycemia or the like while driving, this may cause occurrence of accidents, and thus it is required to measure blood glucose of the driver while driving a vehicle.

A blood glucose measurement method is generally classified into an invasive method, a minimally invasive method, and a noninvasive method. The invasive method is performed by measuring concentration of glucose in blood through a reaction of the glucose with an enzyme. However, it is unable to perform a measurement continuously, and it is required to collect a small amount of blood from a patient for the measurement, causing pain to the patient. The minimally invasive method includes a reverse iontophoresis, and is performed by measuring concentration of glucose existing in subcutaneous interstitial fluid, instead of measuring the concentration of glucose in blood flowing in blood vessels. The concentration of glucose in the subcutaneous interstitial fluid is similar to the concentration of glucose in the blood, but there is a lag time of about six (6) minutes between two concentrations.

The noninvasive method is divided into a non-optical method and an optical method. For the non-optical method, changes in body temperature and movement of body change may lead to large errors in measured values. The optical method includes a method for measuring blood glucose using a photoacoustic effect. The blood glucose measurement method using the photoacoustic effect, according to the related art, uses a neodymium-doped yttrium aluminium garnet (Nd:YAG) laser or an optical parametric oscillator (OPO) tunable laser, which is very expensive and large in size.

SUMMARY

The present disclosure has been made to solve the above-mentioned problems occurring in the prior art while advantages achieved by the prior art are maintained intact.

An aspect of the present disclosure provides a photoacoustic, noninvasive, and continuous blood glucose measurement device that is capable of accurately measuring blood glucose of a driver in a vehicle within a short period of time while driving.

More specifically, inexpensive and compact components, such as a photoacoustic combiner by which a near-infrared pulsed diode laser or a pulsed laser and a photoacoustic wave are allowed to be in a coaxial confocal array, or an optical fiber and a focused ultrasound transducer, may be applied to exemplary embodiments of the present disclosure.

The technical problems to be solved by the present inventive concept are not limited to the aforementioned problems, and any other technical problems not mentioned herein will be clearly understood from the following description by those skilled in the art to which the present disclosure pertains.

According to an aspect of the present disclosure, a photoacoustic, noninvasive, and continuous blood glucose measurement device includes: a diode laser for irradiating a living body with a pulsed laser signal having a specific wavelength; and an ultrasound transducer for measuring a photoacoustic signal in a form of ultrasonic waves generated by a reaction of the living body with the pulsed laser signal.

The device may further include a controller for controlling an operation of the diode laser and for calculating a blood glucose level using the photoacoustic signal measured by the ultrasound transducer.

The controller may control at least one of a pulse width, energy irradiation, and/or a pulse repetition rate of the diode laser.

The device may further include an amplifier for amplifying the photoacoustic signal measured by the ultrasound transducer.

The ultrasound transducer may have a hole, and the hole may have an optical fiber connected to the diode laser.

The device may further include: one or more prisms configured to allow the pulsed laser signal irradiated from the diode laser to be transmitted therethrough; and a silicon oil provided between the one or more prisms, and configured to allow the pulsed laser signal to be transmitted therethrough while allowing the photoacoustic signal to be reflected.

The device may further include an acoustic lens when the ultrasound transducer is an unfocused ultrasound transducer.

The acoustic lens may be disposed at an edge of the one or more prisms.

The diode laser may include: a first diode laser having a first pulse wavelength; and a second diode laser having a second pulse wavelength different from the first pulse wavelength.

The controller may compare a blood glucose value measured by using a pulsed laser signal from the first diode laser with a blood glucose value measured by using a pulsed laser signal from the second diode laser to allow for correction of the measured blood glucose values.

The diode laser and the ultrasound transducer may be provided in at least one of a steering wheel, a gearshift lever, an armrest, a headrest, and/or a rear seat.

The diode laser and the ultrasound transducer may be worn on the living body in a form of a necklace or an in-ear wearable device.

According to another aspect of the present disclosure, a photoacoustic, noninvasive, and continuous blood glucose measurement device includes: a contact part configured to allow part of a living body to contact; a diode laser for irradiating part of the living body with a pulsed laser signal having a specific wavelength; an ultrasound transducer for measuring a photoacoustic signal in a form of ultrasonic waves generated by a reaction of the living body with the pulsed laser signal; one or more one or more prisms configured to allow the pulsed laser signal from the diode laser and the photoacoustic signal to be transmitted therethrough such that the pulsed laser signal and the photoacoustic signal are in a coaxial confocal array; a silicon oil provided between the one or more prisms, and configured to allow the pulsed laser signal to be transmitted therethrough while allowing the photoacoustic signal to be reflected; and a medium part disposed between the contact part and the one or more prisms, and configured to allow the pulsed laser signal and the photoacoustic signal to be transmitted therethrough.

The device may further include an acoustic lens disposed at a top edge of the one or more prism within the medium part.

The ultrasound transducer may include an unfocused ultrasound transducer.

According to another aspect of the present disclosure, a photoacoustic, noninvasive, and continuous blood glucose measurement device includes: a contact part configured to allow part of a living body to contact; a diode laser for irradiating part of the living body with a pulsed laser signal having a specific wavelength; an ultrasound transducer for measuring a photoacoustic signal in a form of ultrasonic waves generated by a reaction of the living body with the pulsed laser signal and configured to allow the pulsed laser signal and the photoacoustic signal to be in a coaxial confocal array; a medium part disposed between the contact part and the ultrasound transducer, and configured to allow the pulsed laser signal and the photoacoustic signal to be transmitted therethrough; and an optical fiber for passing through the ultrasound transducer to be connected to the diode laser.

The ultrasound transducer may include a focused ultrasound transducer.

The ultrasound transducer, the medium part, and the contact part may be inserted into a steering wheel of a vehicle, and the optical fiber and the diode laser may be provided outside of the steering wheel.

The ultrasound transducer, the medium part, and the contact part may be inserted into an in-ear type device, and the optical fiber and the diode laser may be provided at a long distance outside of the in-ear type device.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Figure 1A:
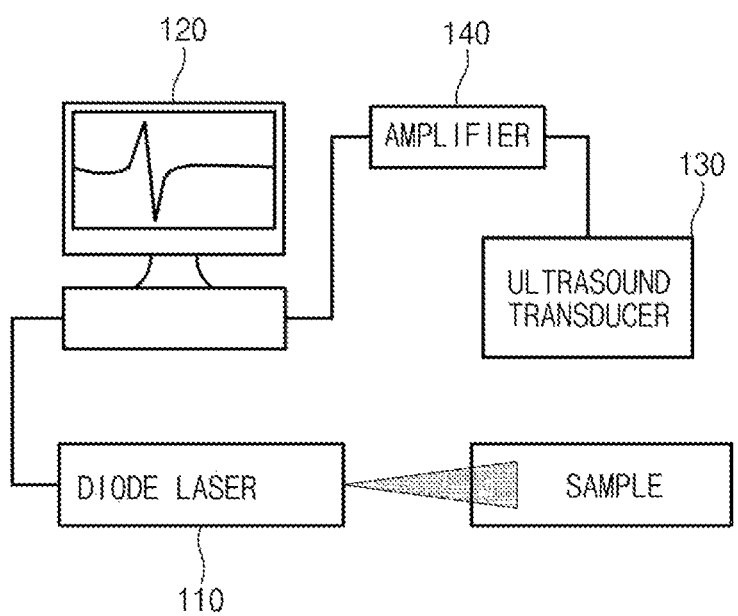
FIG. 1A illustrates the configuration of a photoacoustic, noninvasive, and continuous blood glucose measurement device using a pulsed diode laser, according to an exemplary embodiment of the present disclosure.

Hereinafter, exemplary embodiments of the present disclosure will be described in detail with reference to the accompanying drawings. In the drawings, the same reference numerals will be used throughout to designate the same or equivalent elements. In addition, a detailed description of a related known function or configuration will be ruled out in order not to unnecessarily obscure the gist of the present disclosure.

Terms such as first, second, A, B, (a), and (b) may be used to describe the elements in exemplary embodiments of the present disclosure. These terms are only used to distinguish one element from another element, and the intrinsic features, sequence or order, and the like of the corresponding elements are not limited by the terms. Unless otherwise defined, all terms used herein, including technical or scientific terms, have the same meanings as those generally understood by those with ordinary knowledge in the field of art to which the present disclosure belongs. Such terms as those defined in a generally used dictionary are to be interpreted as having meanings equal to the contextual meanings in the relevant field of art, and are not to be interpreted as having ideal or excessively formal meanings unless clearly defined as having such in the present application.

Hereinafter, exemplary embodiments of the present disclosure will be described in detail with reference to FIGS. 1A to 10.

The present disclosure relates to a photoacoustic blood glucose measurement technology in noninvasive and continuous blood glucose measurement. When a pulsed laser of a specific wavelength is irradiated on the inside of a living body, a substance having high absorption of light with respect to the corresponding wavelength may selectively react with the inside of the living body, causing an increase in temperature for a short period of time and through thermal expansion an ultrasonic wave (ultrasound), which is called a "photoacoustic signal". Therefore, by measuring the photoacoustic signal in a form of ultrasonic waves, the concentration of the substance absorbing the light according to the amplitude of waves (signal) may be back-traced.

FIG. 1A illustrates a configuration of a photoacoustic, noninvasive, and continuous blood glucose measurement device using a pulsed diode laser, according to an exemplary embodiment of the present disclosure.

Referring to FIG. 1A, a photoacoustic, noninvasive, and continuous blood glucose measurement device, according to an exemplary embodiment of the present disclosure, includes a diode laser 110, a controller 120, an ultrasound transducer 130, and an amplifier 140.

The diode laser 110 may irradiate a living body with a pulsed laser (signal) of a specific wavelength.

The controller 120 may be a computer. The controller 120 may control the pulse width, energy irradiation, pulse repetition rate, and the like of the diode laser 110, and calculate a blood glucose level using a photoacoustic signal measured by the ultrasound transducer 130. In other words, the controller 120 may calculate a blood glucose level by tracing back the concentration of a substance absorbing light according to the amplitude of the photoacoustic signal.

The ultrasound transducer 130 may measure the photoacoustic signal in a form of ultrasonic waves generated by the reaction of the living body with the pulsed laser signal.

The amplifier 140 may amplify the photoacoustic signal measured by the ultrasound transducer 130. Here, a single pulse generated by the diode laser 110 may generate a single photoacoustic signal, and in order to increase a signal-to-noise ratio (SNR), 1000 photoacoustic signals may be averaged to obtain a final result.

Figure 1B:
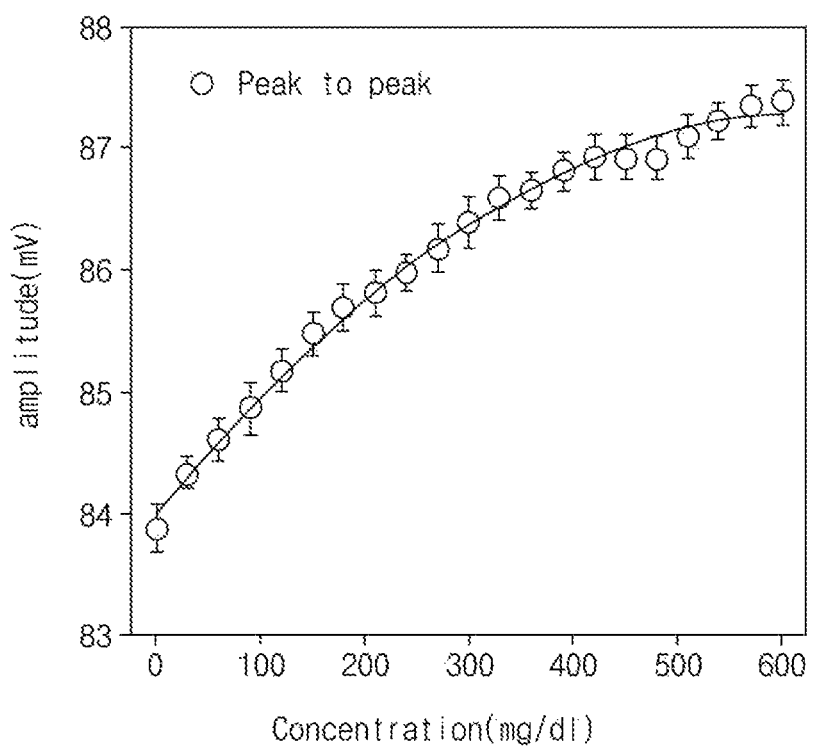
FIG. 1B is a graph illustrating the results of measuring photoacoustic signals with respect to a sample of an aqueous glucose solution of FIG. 1A.

FIG. 1B is a graph illustrating the results of measuring photoacoustic signals with respect to a sample of an aqueous glucose solution of FIG. 1A. Referring to FIG. 1B, as a result of measuring and analyzing peak-to-peak voltages of the photoacoustic signals generated while changing the concentration of the glucose solution in a range of 0 to 600 mg/dL, the amplitude of the signal is increased as the concentration of the glucose solution is increased, as illustrated in the graph of FIG. 1B. In particular, the signal change may be more remarkable at a clinically effective concentration of 200 mg/dL or lower.

The blood glucose measurement method using the photoacoustic signal may use light of wavelengths harmless to human body to improve safety, and may measure the ultrasonic signal to enable the measurement of deeper skin tissue compared to a general optical measurement method. In addition, unlike the general optical measurement method, this method may directly measure the absorption of light by the glucose, thereby achieving high measurement sensitivity.

Figure 2:
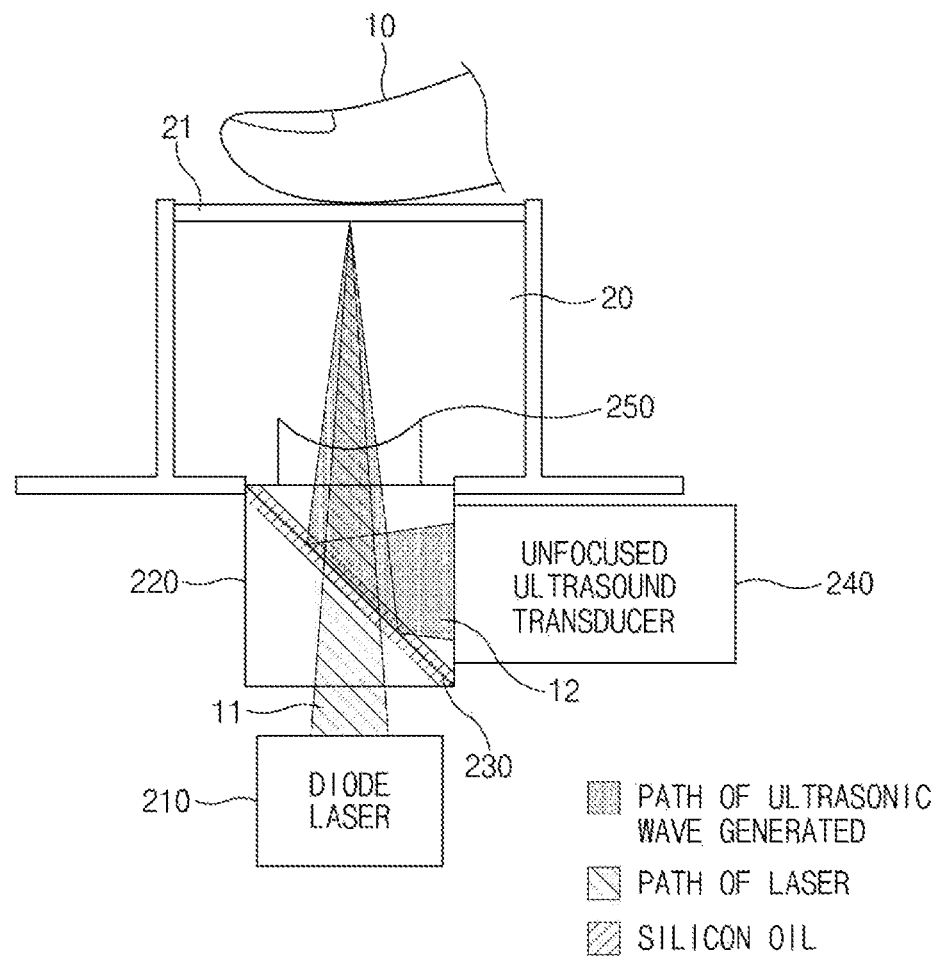
FIG. 2 illustrates the configuration of a photoacoustic, noninvasive, and continuous blood glucose measurement device using a photoacoustic combiner, according to another exemplary embodiment of the present disclosure.

FIG. 2 illustrates the configuration of a photoacoustic, noninvasive, and continuous blood glucose measurement device using a photoacoustic combiner, according to another exemplary embodiment of the present disclosure.

The photoacoustic, noninvasive, and continuous blood glucose measurement device using a photoacoustic combiner, according to an exemplary embodiment of the present disclosure, includes a contact part 21, a medium part 20, a diode laser 210, a plurality of prisms 220, a silicon oil 230, an unfocused ultrasound transducer 240, and an acoustic lens 250.

The contact part 21 may allow part of a living body 10 to contact.

The medium part 20 may be disposed between the contact part 21 and the prisms 220 to allow a pulsed laser signal and a photoacoustic signal to be transmitted therethrough. Here, the medium part 20 includes a medium such as water.

The diode laser 210 may be positioned below the prisms 220 to be spaced apart therefrom by a predetermined gap, and irradiate part of the living body 10 with the pulsed laser signal of a specific wavelength.

The plurality of prisms 220 may be disposed below the medium part 20. One or more prisms may allow the pulsed laser signal and the photoacoustic signal from the diode laser 210 to be transmitted therethrough such that the pulsed laser signal and the photoacoustic signal are in a coaxial confocal array. Here, the coaxial confocal array refers to an array in which a path 11 of the laser signal is the same as a path 12 of the photoacoustic signal, and it may maximize SNR.

The silicon oil 230 may be provided between the plurality of prisms 220 to allow the pulsed laser signal to be transmitted therethrough and allow the photoacoustic signal to be reflected.

The unfocused ultrasound transducer 240 may measure the photoacoustic signal in a form of ultrasonic waves generated by the reaction of the living body with the pulsed laser signal.

The acoustic lens 250 may enable the focusing of the ultrasonic signal even when an inexpensive unfocused transducer is used.

The photoacoustic signal measured by the unfocused ultrasound transducer 240 may be used to measure a blood glucose level through the amplifier 140 and the controller 120 as illustrated in FIG. 1A.

Figure 3:
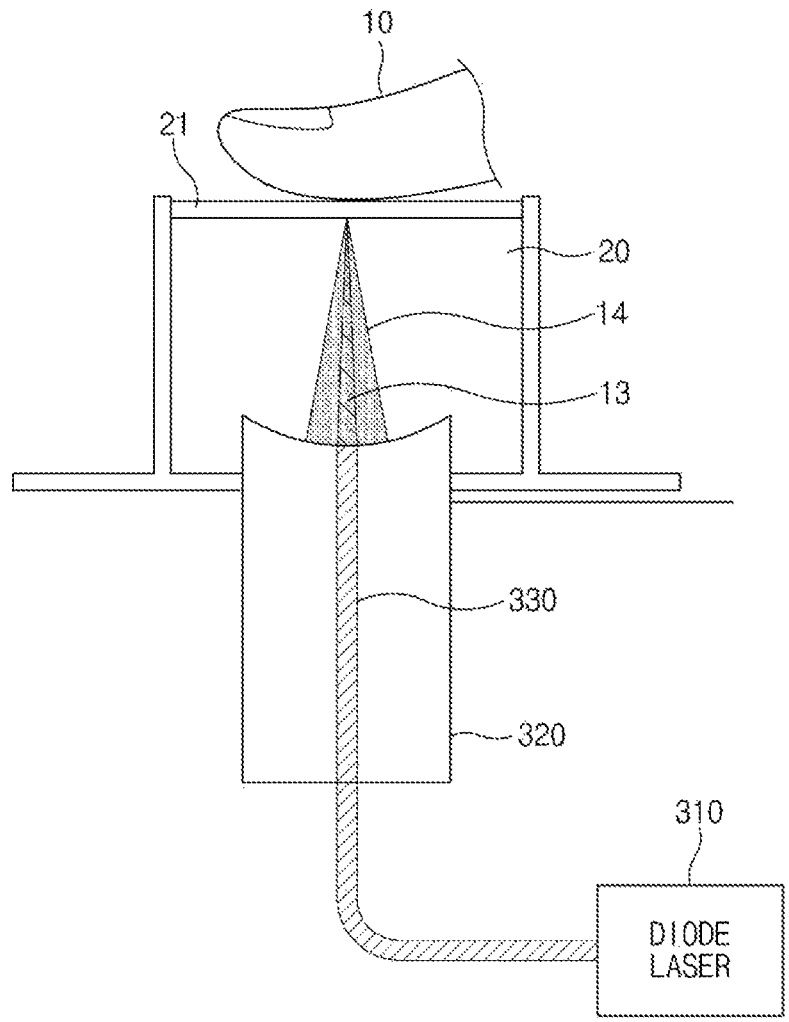
FIG. 3 illustrates the configuration of a photoacoustic, noninvasive, and continuous blood glucose measurement device using an optical fiber and a focused ultrasound transducer, according to another exemplary embodiment of the present disclosure.

FIG. 3 illustrates the configuration of a photoacoustic, noninvasive, and continuous blood glucose measurement device using an optical fiber and a focused ultrasound transducer, according to another exemplary embodiment of the present disclosure.

The photoacoustic, noninvasive, and continuous blood glucose measurement device, according to an exemplary embodiment of the present disclosure, includes the contact part 21, the medium part 20, a diode laser 310, an ultrasound transducer 320, and an optical fiber 330.

The contact part 21 may allow part of the living body 10 to contact.

The medium part 20 may be disposed between the contact part 21 and the ultrasound transducer 320 to allow a pulsed laser signal and a photoacoustic signal to be transmitted therethrough.

The diode laser 310 may be positioned below the ultrasound transducer 320 to be spaced apart therefrom by a predetermined gap, and irradiate part of the living body 10 with the pulsed laser signal of a specific wavelength.

The ultrasound transducer 320 may measure the photoacoustic signal in a form of ultrasonic waves generated by the reaction of the living body with the pulsed laser signal. The ultrasound transducer 320 may have the optical fiber 330 in a central hole thereof.

The optical fiber 330 may transmit light of the diode laser 310 to the living body 10 through the medium part 20.

By using the optical fiber 330, the laser signal may be allowed to be transmitted from far away through the optical fiber 330. In other words, the diode laser may be provided at a long distance and space use of the device may be minimized such that the contact part may be provided inside of a steering wheel and the diode laser may be provided outside of the steering wheel. As illustrated in FIG. 3, a path 13 of the pulsed laser signal may be the same as a path 14 of the photoacoustic signal such that SNR may be maximized.

In addition, the photoacoustic, noninvasive, and continuous blood glucose measurement device, according to an exemplary embodiment of the present disclosure, may allow the contact part 21, the medium part 20, the diode laser 310, the ultrasound transducer 320, the light and the ultrasonic signal to be in the coaxial confocal array, thereby increasing the SNR.

The photoacoustic signal measured by the ultrasound transducer 320 may be used to measure a blood glucose level through the amplifier 140 and the controller 120 as illustrated in FIG. 1A.

Figure 4A:
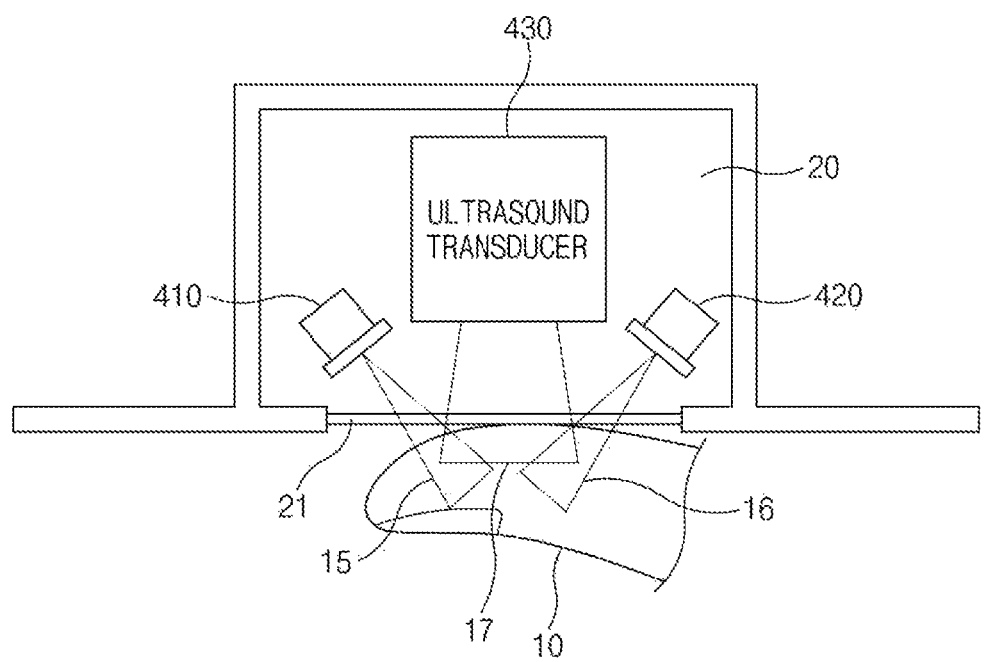
FIG. 4A illustrates the configuration of a photoacoustic, noninvasive, and continuous blood glucose measurement device using a plurality of diode lasers having different wavelengths, according to another exemplary embodiment of the present disclosure.
Figure 4B:
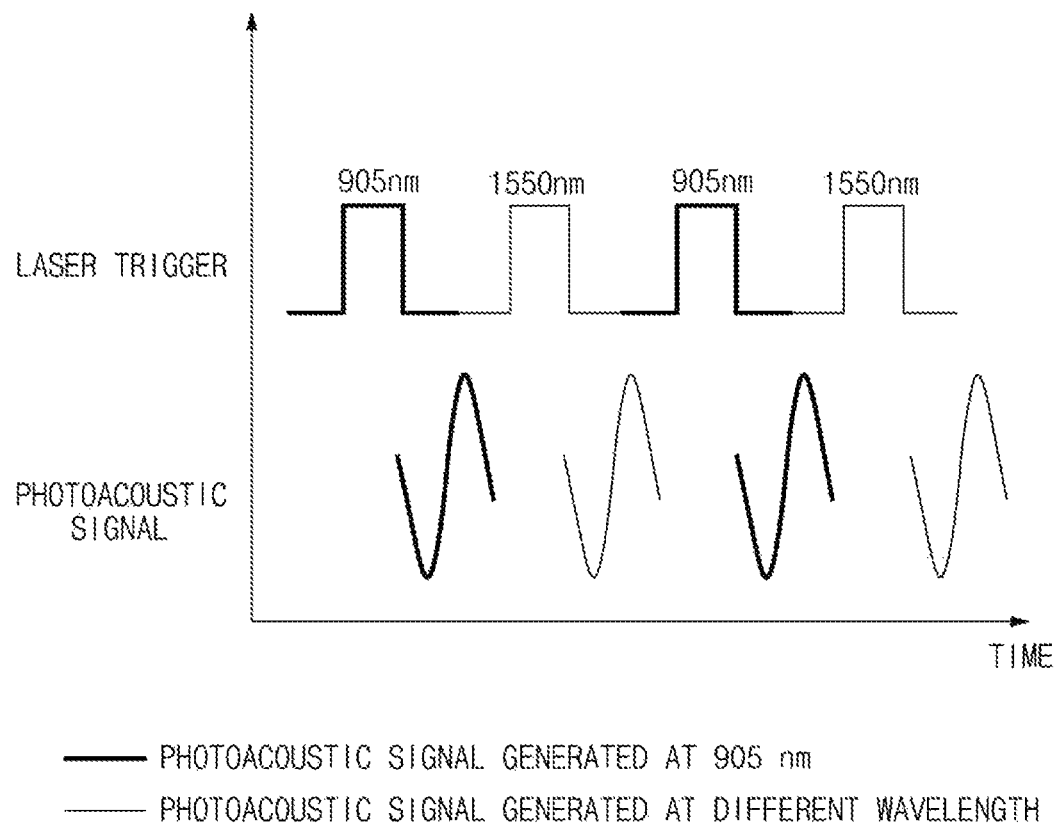
FIG. 4B is a graph illustrating the results of measuring photoacoustic signals by the plurality of diode lasers having different wavelengths of FIG. 4A.

FIG. 4A illustrates the configuration of a photoacoustic, noninvasive, and continuous blood glucose measurement device using a plurality of diode lasers having different wavelengths, according to another exemplary embodiment of the present disclosure, and FIG. 4B is a graph illustrating the results of measuring photoacoustic signals by the plurality of diode lasers having different wavelengths of FIG. 4A.

Referring to FIG. 4A, the photoacoustic, noninvasive, and continuous blood glucose measurement device, according to an exemplary embodiment of the present disclosure, includes the contact part 21, the medium part 20, and a first diode laser 410, a second diode laser 420, and an ultrasound transducer 430 which are provided in different positions within the medium part 20.

The first diode laser 410 may provide a pulsed laser signal 15 having a wavelength of 905 nm.

The second diode laser 420 may provide a pulsed laser signal 16 having a wavelength of 1550 nm.

The ultrasound transducer 430 may measure a photoacoustic signal 17 in a form of ultrasonic waves generated through the reaction of a living body with the pulsed laser signals.

By simultaneously using the first diode laser 410 and the second diode laser 420 providing lasers at different wavelengths at which the absorption of light by glucose differs, this may allow for correction of glucose concentration measured values. In other words, a blood glucose level measured using the pulsed laser signal from the first diode laser 410 and a blood glucose level measured using the pulsed laser signal from the second diode laser 420 may be compared to each other to identify an error value, and thus appropriate correction may be made.

The photoacoustic signal measured by the ultrasound transducer 430 may be used to measure a blood glucose level through the amplifier 140 and the controller 120 as illustrated in FIG. 1A.

Figure 5:
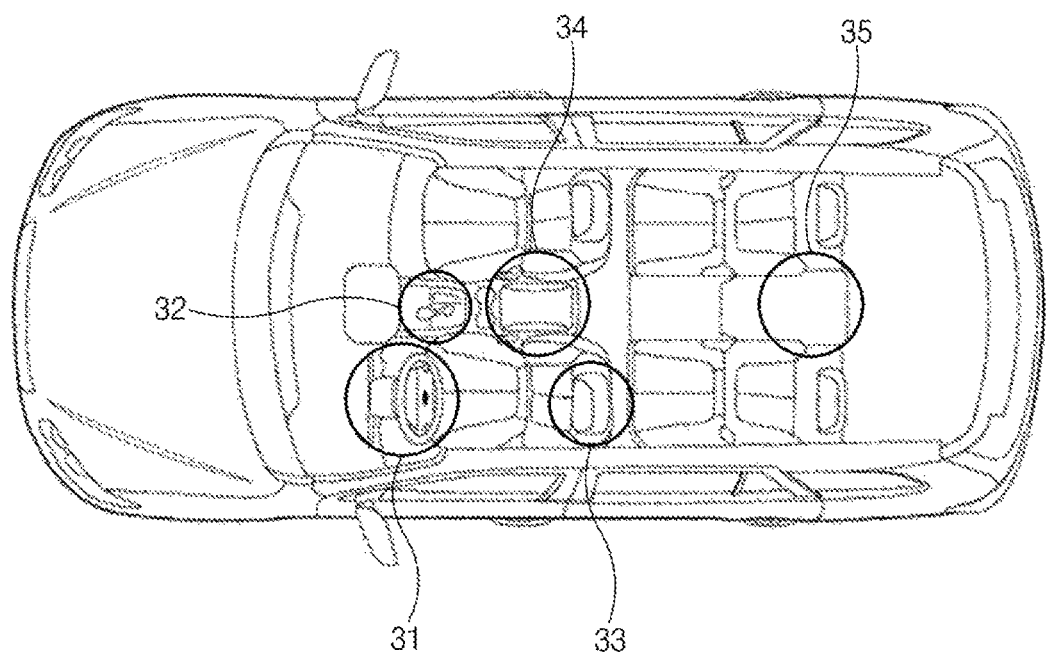
FIG. 5 illustrates the position(s) of a photoacoustic, noninvasive, and continuous blood glucose measurement device mounted in a vehicle, according to exemplary embodiments of the present disclosure.

FIG. 5 illustrates the position(s) of a photoacoustic, noninvasive, and continuous blood glucose measurement device mounted in a vehicle, according to exemplary embodiments of the present disclosure.

Referring to FIG. 5, part of a driver's body that can be subject to blood glucose measurement while driving in the vehicle may be a hand and a face of which the skin is always exposed. A place appropriate for ease of installation of the blood glucose measurement device in order to measure a photoacoustic signal from the hand may be a steering wheel 31, a gearshift 32, and an arm rest 34. In order to measure a photoacoustic signal from part of the face, a place appropriate for installation of the blood glucose measurement device may be a headrest 33 of a driver's seat. When the photoacoustic signal is measured from part of the face, a blood glucose value may be measured accurately on the grounds that the driver makes the least amount of movement while driving since the body is fixed. In addition, in order to measure the blood glucose of a passenger in the vehicle, the blood glucose measurement device may be provided on an armrest 35 in the middle of a rear seat.

Figure 6:
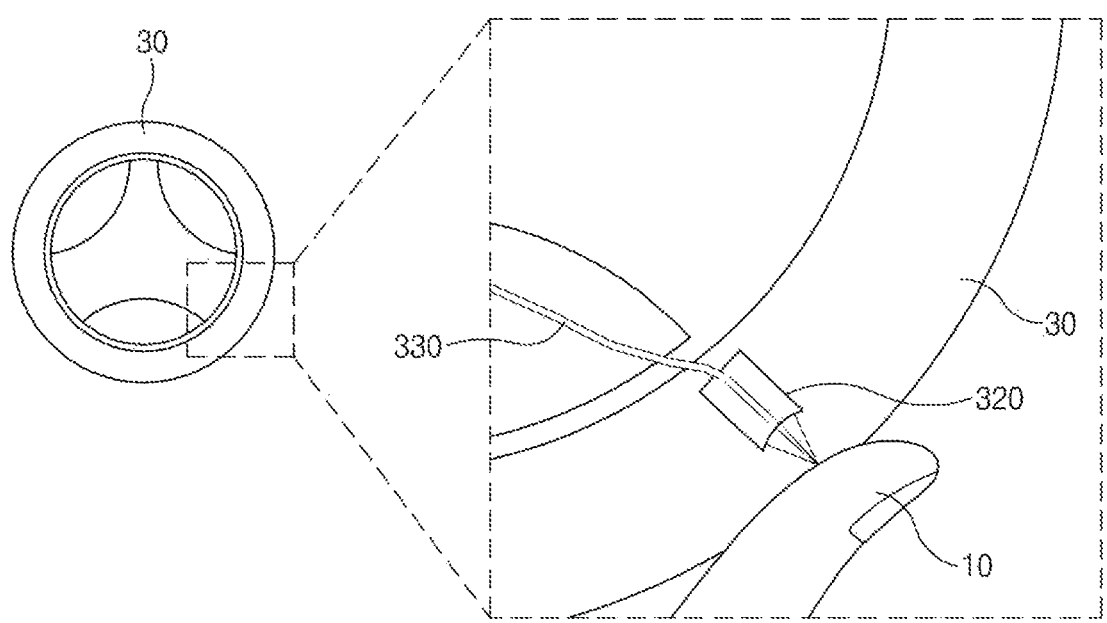
FIG. 6 illustrates an example of measuring a blood glucose level using a blood glucose measurement device mounted in a steering wheel, according to an exemplary embodiment of the present disclosure.

FIG. 6 illustrates an example of measuring a blood glucose level using a blood glucose measurement device mounted in a steering wheel, according to an exemplary embodiment of the present disclosure. Referring to FIG. 6, in order to allow a patient with diabetes to continuously measure blood glucose levels while driving a vehicle, the blood glucose measurement device may be mounted inside a steering wheel 30 to which bare skin is exposed for the longest period of time. Here, by allowing the optical fiber 330 to pass through the central hole of the ultrasound transducer 320 to transmit light, the contact part, the medium part, and the ultrasound transducer may be mounted inside the steering wheel, while the diode laser and the signal amplifier may be provided in a separate space outside of the steering wheel.

Figure 7:
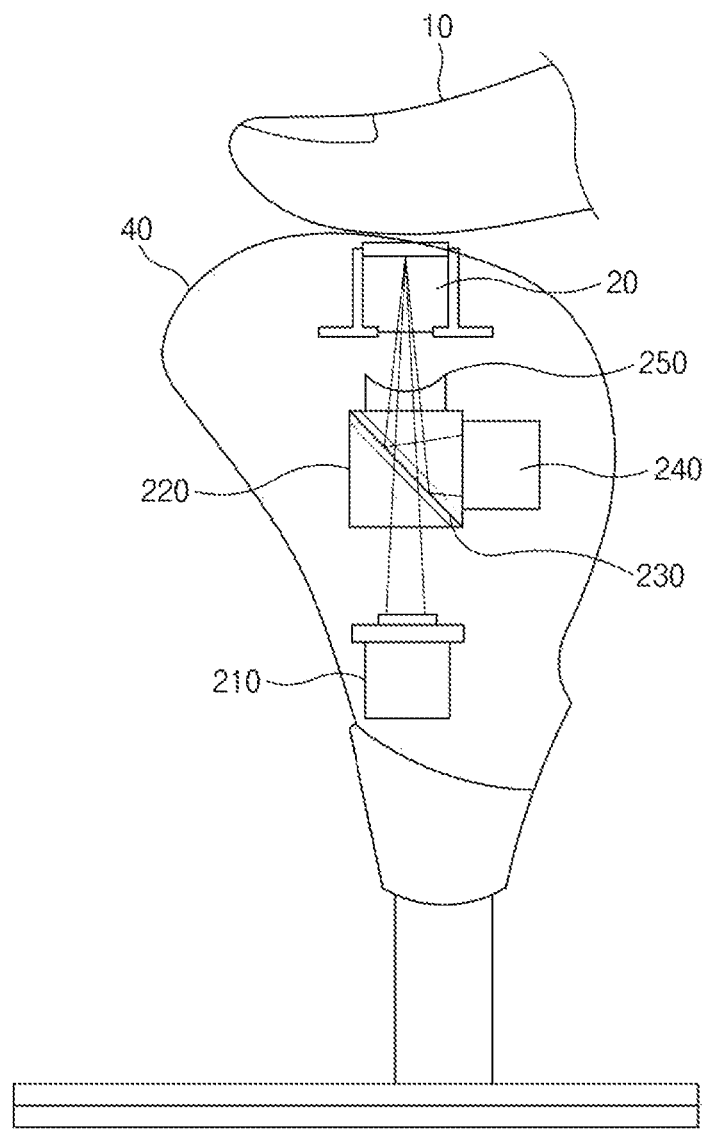
FIG. 7 illustrates an example of measuring a blood glucose level using a blood glucose measurement device mounted in a gearshift lever, according to an exemplary embodiment of the present disclosure.
Figure 8:
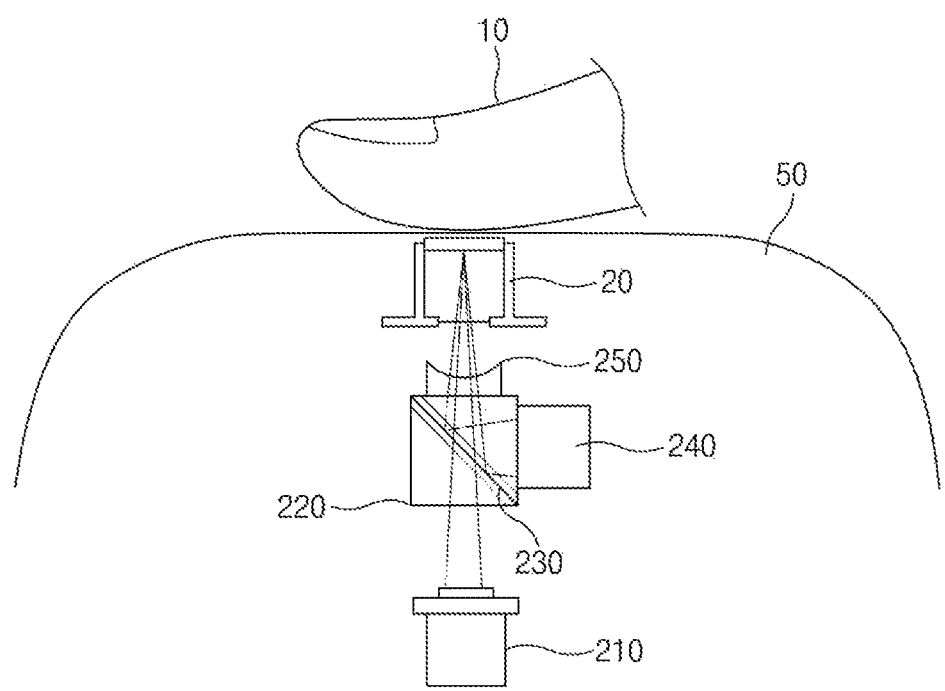
FIG. 8 illustrates an example of measuring a blood glucose level using a blood glucose measurement device mounted in a rear seat, according to an exemplary embodiment of the present disclosure.

FIG. 7 illustrates an example of measuring a blood glucose level using a blood glucose measurement device mounted in a gearshift lever, according to an exemplary embodiment of the present disclosure, and FIG. 8 illustrates an example of measuring a blood glucose level using a blood glucose measurement device mounted in a rear seat, according to an exemplary embodiment of the present disclosure.

Referring to FIGS. 7 and 8, the blood glucose measurement device, according to an exemplary embodiment of FIG. 2, may be mounted in a gearshift lever 40 and in a rear seat armrest 50. Alternatively, the blood glucose measurement device having the structure illustrated in FIG. 3 or FIG. 4A may also be mounted in the gearshift lever 40 and in the rear seat armrest 50.

Through the installation of the blood glucose measurement device including the photoacoustic combiner illustrated in FIG. 2, which is easy to be fixed to the aforementioned places, the path of the photoacoustic signal and the path of the laser signal may be in the coaxial confocal array, and thus the SNR may be increased.

Figure 9A:
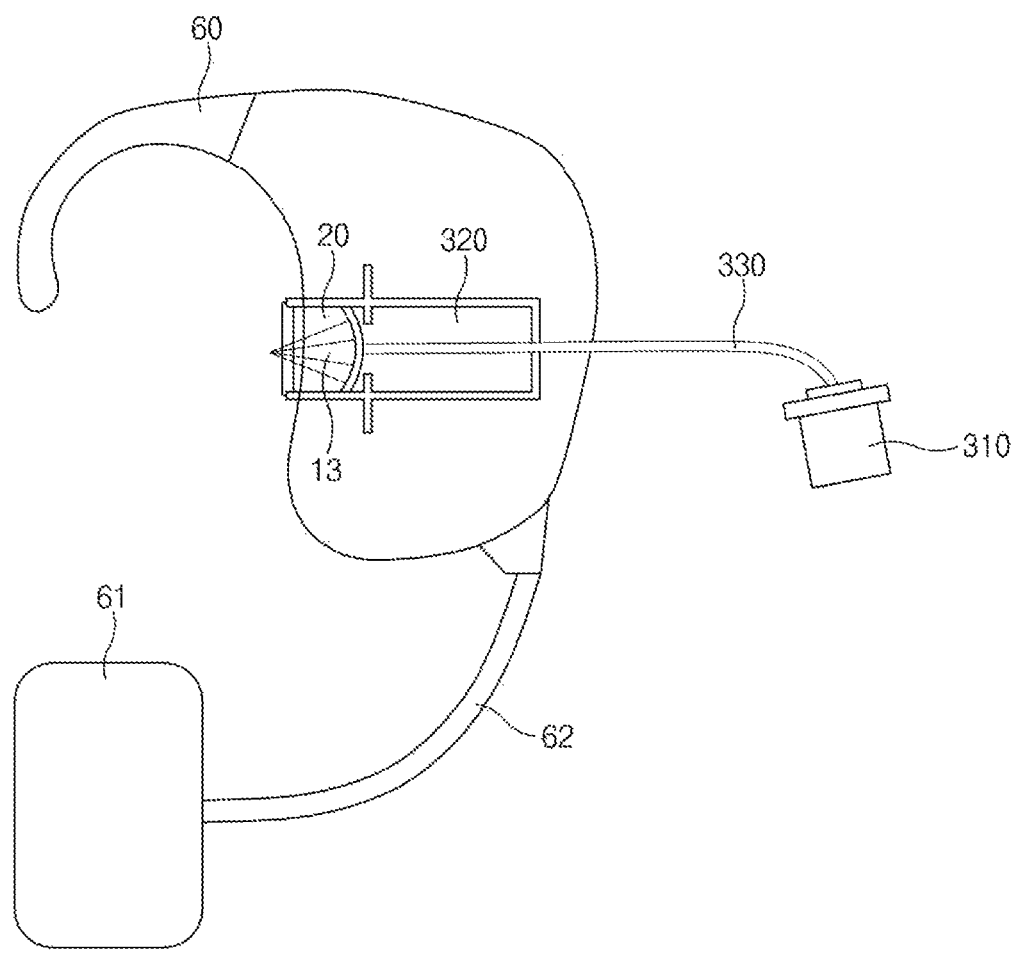
FIG. 9A illustrates the configuration of an in-ear type blood glucose measurement device, according to an exemplary embodiment of the present disclosure.
Figure 9B:
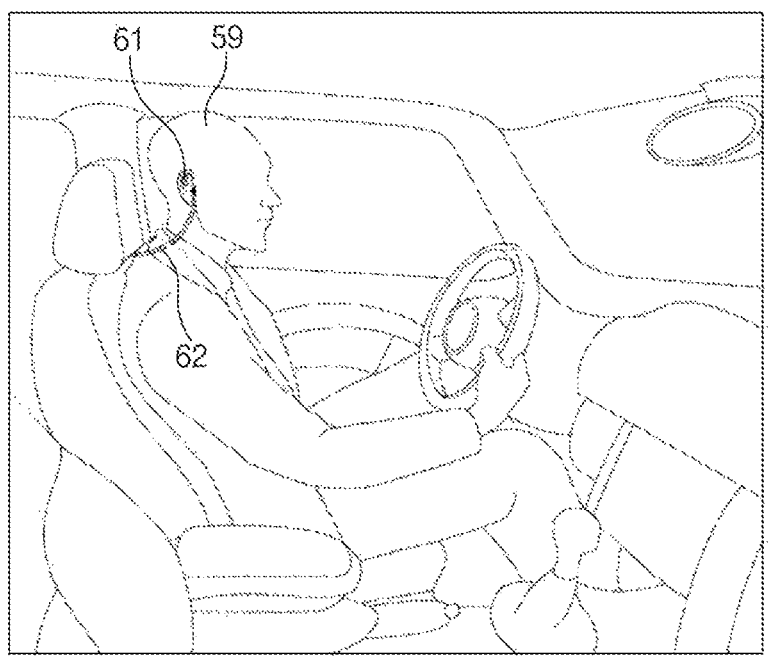
FIG. 9B illustrates a driver wearing the in-ear type blood glucose measurement device of FIG. 9A.

FIG. 9A illustrates an in-ear type blood glucose measurement device according to an exemplary embodiment of the present disclosure, and FIG. 9B illustrates a driver wearing the in-ear type blood glucose measurement device of FIG. 9A.

Besides the hand of the driver, a photoacoustic signal may be measured from part of the face, ear, and/or neck of the driver which is exposed for a long period of time while driving. The driver may wear a blood glucose measurement device in a form of an in-ear or a necklace wearable device on the corresponding part(s) of the living body to measure a blood glucose concentration while driving.

Referring to FIG. 9A, the blood glucose measurement device including an optical fiber may be inserted into an in-ear wearable device, which includes an ear hook 60, a fixing part 61, and a cable 62 connected to a body of the device.

As described above, the present disclosure relates to a noninvasive and continuous blood glucose measurement technology using a photoacoustic effect, which allows the driver to measure the blood glucose level quickly, conveniently, and accurately.

Figure 10:
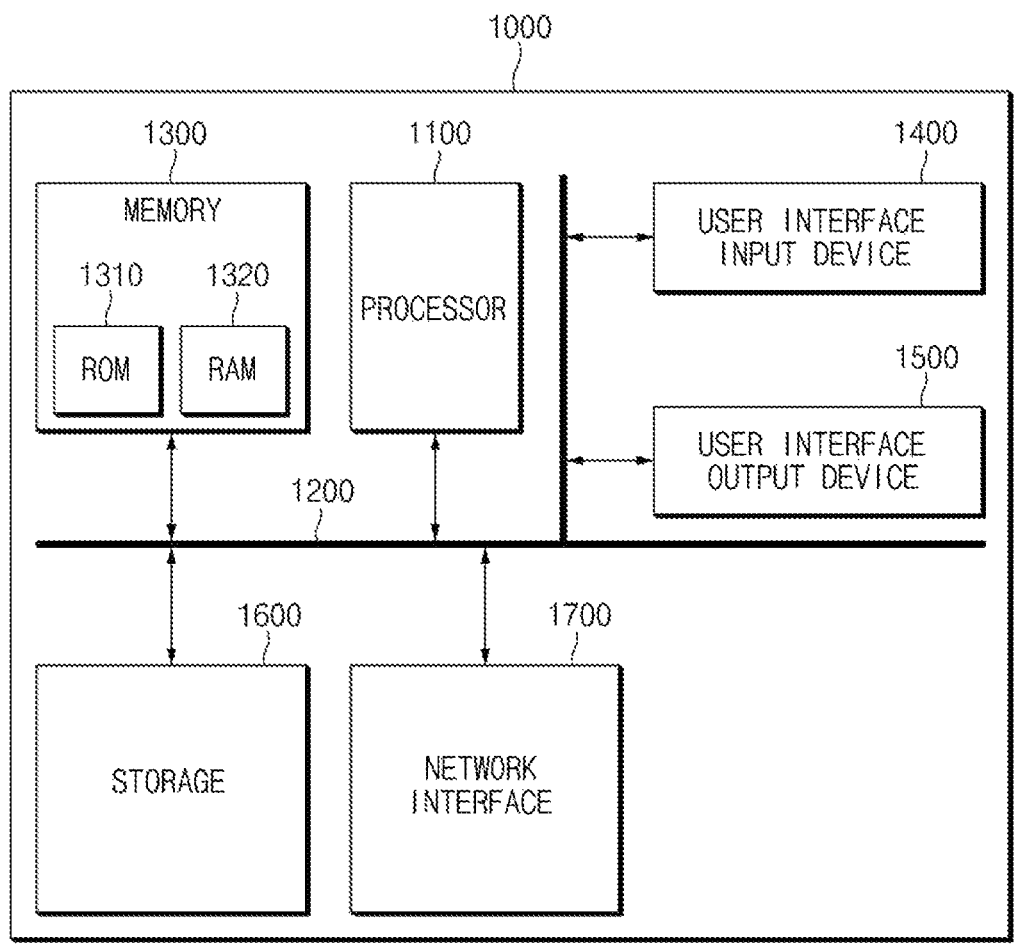
FIG. 10 illustrates the configuration of a computing system by which a photoacoustic, noninvasive, and continuous blood glucose measurement method according to an exemplary embodiment of the present disclosure is executed.

FIG. 10 illustrates the configuration of a computing system by which a photoacoustic, noninvasive, and continuous blood glucose measurement method according to an exemplary embodiment of the present disclosure is executed.

Referring to FIG. 10, a computing system 1000 includes at least one processor 1100, a bus 1200, a memory 1300, a user interface input device 1400, a user interface output device 1500, a storage 1600, and a network interface 1700, wherein these elements are connected through the bus 1200.

The processor 1100 may be a central processing unit (CPU) or a semiconductor device processing commands stored in the memory 1300 and/or the storage 1600. The memory 1300 and the storage 1600 include various types of volatile or non-volatile storage mediums. For example, the memory 1300 includes a read only memory (ROM) and a random access memory (RAM).

Therefore, the steps of the method or algorithm described in connection with the exemplary embodiments disclosed herein may be embodied directly in a hardware module or a software module that is executed by the processor 1100, or a combination of both. The software module may reside in storage mediums, i.e., the memory 1300 and/or the storage 1600, such as RAM, a flash memory, ROM, an erasable programmable read-only memory (EPROM), an electrically erasable programmable read-only memory (EEPROM), a register, a hard disk, a removable disk, and a CD-ROM.

The exemplary storage medium may be coupled to the processor 1100, such that the processor 1100 may read information from the storage medium and write information to the storage medium. Alternatively, the storage medium may be integrated with the processor 1100. The processor 1100 and the storage medium may reside in an application specific integrated circuit (ASIC). The ASIC may reside in a user terminal. Alternatively, the processor 1100 and the storage medium may reside as individual components in a user terminal.

As set forth above, the present inventive concept may allow the driver to measure the blood glucose level accurately by mounting the inexpensive noninvasive and continuous blood glucose measurement device in the vehicle, thereby preventing accidents that may be caused by hypoglycemic shock of the driver with diabetes during driving.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. A photoacoustic, noninvasive, and continuous blood glucose measurement device, comprising:
    a diode laser for irradiating a living body with a pulsed laser signal having a specific wavelength;
    an ultrasound transducer for measuring a photoacoustic signal in a form of ultrasonic waves generated by a reaction of the living body with the pulsed laser signal;
    a contact part configured to contact part of a living body;
    a medium part disposed between the contact part and the ultrasound transducer, and configured to transmit the pulsed laser signal and the photoacoustic signal therethrough; and
    an optical fiber for passing through the ultrasound transducer to be connected to the diode laser,
    wherein the diode laser and the optical fiber are disposed outside of a steering wheel of a vehicle and in at least one of a gearshift lever, an armrest, a headrest, or a rear seat, and
    the ultrasound transducer, the medium part, and the contact part are mounted inside the steering wheel of the vehicle.

2. The photoacoustic, noninvasive, and continuous blood glucose measurement device according to claim 1,
    wherein the ultrasound transducer is configured to allow the pulsed laser signal and the photoacoustic signal to be in a coaxial confocal array.

3. The photoacoustic, noninvasive, and continuous blood glucose measurement device according to claim 2, wherein the ultrasound transducer is a focused ultrasound transducer.

* * * * *